US009215869B1

United States Patent
Adang et al.

(10) Patent No.: US 9,215,869 B1
(45) Date of Patent: Dec. 22, 2015

(54) NON-CADHERIN POLYPEPTIDE POTENTITATORS OF CRY PROTEINS

(75) Inventors: Michael J. Adang, Athens, GA (US); Rui Zhang, Gainsville, FL (US); Gang Hua, Athens, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 186 days.

(21) Appl. No.: 13/090,830

(22) Filed: Apr. 20, 2011

Related U.S. Application Data

(60) Provisional application No. 61/325,944, filed on Apr. 20, 2010.

(51) Int. Cl.
*A01N 37/18* (2006.01)

(52) U.S. Cl.
CPC ....................................... *A01N 37/18* (2013.01)

(58) Field of Classification Search
None
See application file for complete search history.

(56) References Cited

U.S. PATENT DOCUMENTS

| 7,011,975 | B1 | 3/2006 | Adang et al. |
| 8,101,568 | B2 | 1/2012 | Adang et al. |

FOREIGN PATENT DOCUMENTS

| WO | WO 2009/124258 | * | 8/2009 |

OTHER PUBLICATIONS

Hua et al ('Anopheles gambiae cadherin AgCad1 binds the cry4ba toxin of bacillus thuringiensis israelensis and a fragment of agcad1 synergizes toxicity' Biochemistry 2008 v47 pp. 5101-5110).*
Zhang et al ('Synergistic and inhibitory effects of aminopeptidase peptides on bacillus thuringiensis cry11ba toxicity in the mosquito anopheles gambiae' Biochemistry 2010 v49 pp. 8512-8519).*
Insecticide definition retrieved from http://organic.about.com/od/organicdefinitionsij/g/Insecticide.htm on Nov. 14, 2013, 1 page.*
Fillinger et al ('Efficacy and efficiency of new *Bacillus thuringiensis* var. *israielensis* and Bacillus sphaericus formulations against Afrotropical anophelines in Western Kenya' Tropical Medicine and International Health v8(1) Jan. 2003 pp. 37-47).*
Vectobac product sheet (retrieved from http://publichealth.valentbiosciences.com/docs/resources/vectobac-wdg-specimen-label.pdf on Jan. 8, 2015, 2 pages).*
Chen, J. et al, "Synergism of *Bacillus thuringiensis* toxins by a fragment of a toxin-binding cadherin," Proc. Natl. Acad. Sci., Aug. 28, 2007, pp. 13901-13906, vol. 104, Issue 35, USA.
Nakanishi, K. et al., "Aminopeptidase N isoforms from the midgut of *Bumbyx mori* and *Plutella xylostella*—their classification and the factors that determine their binding specificity to *Bacillus thuringiensis* Cry1A toxin," FEBS Letters 519, Apr. 23, 2002, pp. 215-220, FEBS 26077.
Yaoi, K. et al., "*Bacillus thuringiensis* Cry1Aa toxin-binding region of *Bombyx mori* aminopeptidase N," FEBS Letters 463, Nov. 16, 1999, pp. 221-224, FEBS 23056.
Park, Y. et al., "Enhancement of *Bacillus thuringiensis* Cry3Aa and Cry3Bb Toxicities to Coleopteran Larvae by a Toxin-Binding Fragment of an insect Cadherin," Applied and Environmental Microbiology, Mar. 27, 2009, pp. 3085-3092, vol. 75, Issue 10.
Park, Y. et al., "Cadherin Fragments from *Anopheles gambiae* Synergize *Bacillus thuringiensis* Cry4Ba's Toxicity against *Aedes aegypti* Larvae," Applied and Environmental Microbiology, Oct. 2, 2009, pp. 7279-7282, vol. 75, Issue 22.
Masson, L. et al., "The Cry IA(c) Receptor Purified from *Manduca sexta* Displays Multiple Specificities," J. Biol. Chem., Sep. 1, 1995, pp. 20309-20315, vol. 270, Issue 35, USA.
Pigott, C.R., et al., "Role of Receptors in *Bacillus thuringiensis* Crystal Toxin Activity," Microbiology and Molecular Biology Review, 2007, pp. 254-281, vol. 71, Issue 2.
Zhang, R. et al., "A 106-kDa aminopeptidase is a putative receptor for *Bacillus thuringiensis* Cry11Ba toxin in the mosquito *Anopheles gambiae*," Biochemistry, Oct. 28, 2008, pp. 11263-11272, vol. 47, Issue 43.

\* cited by examiner

*Primary Examiner* — Karlheinz R Skowronek
*Assistant Examiner* — Ronald Niebauer
(74) *Attorney, Agent, or Firm* — Faegre Baker Daniels LLP

(57) ABSTRACT

The subject invention relates in part to fragments of non-cadherin Cry toxin binding proteins, wherein the fragments potentiate, or act as synergists with, the insecticidal activity of Cry proteins. In some preferred embodiments, the binding protein (a Cry protein receptor on insect midgut cells) is an aminopeptidase. In preferred embodiments, the fragment comprises a Cry protein binding region.

1 Claim, 7 Drawing Sheets

SEQUENCE LISTING

```
<160> NUMBER OF SEQ ID NOS: 15

<210> SEQ ID NO 1
<211> LENGTH: 724
<212> TYPE: PRT
<213> ORGANISM: Bacillus thuringiensis

<400> SEQUENCE: 1

Met Gln Asn Asn Asn Phe Asn Thr Thr Glu Ile Asn Asn Met Ile Asn
1               5                   10                  15

Phe Pro Met Tyr Asn Gly Arg Leu Glu Pro Ser Leu Ala Pro Ala Leu
            20                  25                  30

Ile Ala Val Ala Pro Ile Ala Lys Tyr Leu Ala Thr Ala Leu Ala Lys
        35                  40                  45

Trp Ala Val Lys Gln Gly Phe Ala Lys Leu Lys Ser Glu Ile Phe Pro
50                  55                  60

Gly Asn Thr Pro Ala Thr Met Asp Lys Val Arg Ile Glu Val Gln Thr
65                  70                  75                  80

Leu Leu Asp Gln Arg Leu Gln Asp Asp Arg Val Lys Ile Leu Glu Gly
                85                  90                  95

Glu Tyr Lys Gly Ile Ile Asp Val Ser Lys Val Phe Thr Asp Tyr Val
            100                 105                 110

Asn Gln Ser Lys Phe Glu Thr Gly Thr Ala Asn Arg Leu Phe Phe Asp
        115                 120                 125

Thr Ser Asn Gln Leu Ile Ser Arg Leu Pro Gln Phe Glu Ile Ala Gly
    130                 135                 140

Tyr Glu Gly Val Ser Ile Ser Leu Phe Thr Gln Met Cys Thr Phe His
145                 150                 155                 160

Leu Gly Leu Leu Lys Asp Gly Ile Leu Ala Gly Ser Asp Trp Gly Phe
                165                 170                 175

Ala Pro Ala Asp Lys Asp Ala Leu Ile Cys Gln Phe Asn Arg Phe Val
            180                 185                 190

Asn Glu Tyr Asn Thr Arg Leu Met Val Leu Tyr Ser Lys Glu Phe Gly
        195                 200                 205

Arg Leu Leu Ala Lys Asn Leu Asn Glu Ala Leu Asn Phe Arg Asn Met
    210                 215                 220

Cys Ser Leu Tyr Val Phe Pro Phe Ser Glu Ala Trp Ser Leu Leu Arg
225                 230                 235                 240

Tyr Glu Gly Thr Lys Leu Glu Asn Thr Leu Ser Leu Trp Asn Phe Val
                245                 250                 255

Gly Glu Ser Ile Asn Asn Ile Ser Pro Asn Asp Trp Lys Gly Ala Leu
            260                 265                 270

Tyr Lys Leu Leu Met Gly Ala Pro Asn Gln Arg Leu Asn Asn Val Lys
        275                 280                 285

Phe Asn Tyr Ser Tyr Phe Ser Asp Thr Gln Ala Thr Ile His Arg Glu
    290                 295                 300

Asn Ile His Gly Val Leu Pro Thr Tyr Asn Gly Gly Pro Thr Ile Thr
305                 310                 315                 320
```

```
Gly Trp Ile Gly Asn Gly Arg Phe Ser Gly Leu Ser Phe Pro Cys Ser
            325                 330                 335

Asn Glu Leu Glu Ile Thr Lys Ile Lys Gln Glu Ile Thr Tyr Asn Asp
            340                 345                 350

Lys Gly Gly Asn Phe Asn Ser Ile Val Pro Ala Ala Thr Arg Asn Glu
            355                 360                 365

Ile Leu Thr Ala Thr Val Pro Thr Ser Ala Asp Pro Phe Phe Lys Thr
            370                 375                 380

Ala Asp Ile Asn Trp Lys Tyr Phe Ser Pro Gly Leu Tyr Ser Gly Trp
385                 390                 395                 400

Asn Ile Lys Phe Asp Asp Thr Val Thr Leu Lys Ser Arg Val Pro Ser
            405                 410                 415

Ile Ile Pro Ser Asn Ile Leu Lys Tyr Asp Asp Tyr Tyr Ile Arg Ala
            420                 425                 430

Val Ser Ala Cys Pro Lys Gly Val Ser Leu Ala Tyr Asn His Asp Phe
            435                 440                 445

Leu Thr Leu Thr Tyr Asn Lys Leu Glu Tyr Asp Ala Pro Thr Thr Gln
            450                 455                 460

Asn Ile Ile Val Gly Phe Ser Pro Asp Asn Thr Lys Ser Phe Tyr Arg
465                 470                 475                 480

Ser Asn Ser His Tyr Leu Ser Thr Thr Asp Asp Ala Tyr Val Ile Pro
            485                 490                 495

Ala Leu Gln Phe Ser Thr Val Ser Asp Arg Ser Phe Leu Glu Asp Thr
            500                 505                 510

Pro Asp Gln Ala Thr Asp Gly Ser Ile Lys Phe Thr Asp Thr Val Leu
            515                 520                 525

Gly Asn Glu Ala Lys Tyr Ser Ile Arg Leu Asn Thr Gly Phe Asn Thr
            530                 535                 540

Ala Thr Arg Tyr Arg Leu Ile Ile Arg Phe Lys Ala Pro Ala Arg Leu
545                 550                 555                 560

Ala Ala Gly Ile Arg Val Arg Ser Gln Asn Ser Gly Asn Asn Lys Leu
            565                 570                 575

Leu Gly Gly Ile Pro Val Glu Gly Asn Ser Gly Trp Ile Asp Tyr Ile
            580                 585                 590

Thr Asp Ser Phe Thr Phe Asp Asp Leu Gly Ile Thr Thr Ser Ser Thr
            595                 600                 605

Asn Ala Phe Phe Ser Ile Asp Ser Asp Gly Val Asn Ala Ser Gln Gln
            610                 615                 620

Trp Tyr Leu Ser Lys Leu Ile Leu Val Lys Glu Ser Ser Phe Thr Thr
625                 630                 635                 640

Gln Ile Pro Leu Lys Pro Tyr Val Ile Val Arg Cys Pro Asp Thr Phe
            645                 650                 655

Phe Val Ser Asn Asn Ser Ser Ser Thr Tyr Glu Gln Gly Tyr Asn Asn
            660                 665                 670

Asn Tyr Asn Gln Asn Ser Ser Met Tyr Asp Gln Gly Tyr Asn Asn
            675                 680                 685

Ser Tyr Asn Pro Asn Ser Gly Cys Thr Cys Asn Gln Asp Tyr Asn Asn
            690                 695                 700

Ser Tyr Asn Gln Asn Ser Gly Cys Thr Cys Asn Gln Gly Tyr Asn Asn
705                 710                 715                 720

Asn Tyr Pro Lys

<210> SEQ ID NO 2
```

```
<211> LENGTH: 935
<212> TYPE: PRT
<213> ORGANISM: Anopheles gambiae

<400> SEQUENCE: 2

Met Thr Leu Ala Glu Lys Leu Ala Leu Val Val Leu Thr Cys Ala
1               5                   10                  15

Cys Ala Val Val Ser Thr Ala Ser Pro Leu Asp Pro Asp Arg Tyr Phe
            20                  25                  30

Leu Val Glu Ala Glu Pro Arg Ala Gln Pro Glu Asp Tyr Arg Leu Asn
                35                  40                  45

Asp Asp Val Trp Pro Thr His Tyr Asp Ile Glu Ile Lys Pro Tyr Leu
        50                  55                  60

Glu Gln Glu Gly Asn Lys Ala Gln Phe Thr Phe Asp Gly Ser Ala Lys
65                  70                  75                  80

Ile Thr Val Ser Thr Gln Lys Gln Asn Val Met Gln Ile Lys Leu His
                85                  90                  95

Met Ala Arg Met Asp Ile Thr Ala Trp Ser Val Thr Lys Ser Asp
                100                 105                 110

Asn Thr Ile Ile Pro Thr Leu Pro Gln Thr Tyr Asp Gln Glu Thr Gln
                115                 120                 125

Ile Leu Thr Leu Pro Leu Ser Ser Ala Leu Gln Ala Asn Val Glu Tyr
        130                 135                 140

Val Leu Ser Phe Thr Tyr Val Gly Asn Met Asp Asp Met His Gly
145                 150                 155                 160

Phe Tyr Arg Ser Tyr Tyr Trp Glu Asp Gly Val Lys Val Trp Met Gly
                165                 170                 175

Ser Thr Gln Phe Gln Gln Thr His Ala Arg Arg Ala Phe Pro Cys Phe
                180                 185                 190

Asp Glu Pro Arg Phe Lys Ala Thr Phe Gln Leu Lys Ile Asn His Lys
                195                 200                 205

Thr Gln Tyr Asn Val Tyr Ser Asn Thr Ala Ile Val Gly Thr Ala Val
        210                 215                 220

Ala Glu Val Gly Arg Ser Leu Thr Thr Phe Gly Val Thr Pro Ser Met
225                 230                 235                 240

Ser Ser Tyr Leu Ile Ala Phe Ile Val Ala Pro Tyr Gln Ile Asn Asp
                245                 250                 255

Arg Asp Gly Met Gly Ile Leu Ala Arg Pro Gln Ala Gln Asn Gln Thr
                260                 265                 270

Gln Tyr Ser Leu Asp Val Gly Ile Lys Leu Leu Lys Ala Leu Glu Glu
        275                 280                 285

Trp Ile Asp Tyr Pro Tyr Ala Ser Val Ala Gly Met Thr Arg Met Tyr
    290                 295                 300

Met Ala Ala Val Pro Asp Phe Ser Ala Gly Ala Met Glu Asn Trp Gly
305                 310                 315                 320

Leu Leu Thr Tyr Arg Glu Thr Asn Ile Leu Tyr Arg Ser Asp Asp Ser
                325                 330                 335

Thr Ser Met Gln Gln His Arg Ile Ala Ala Val Ile Ser His Glu Ile
                340                 345                 350

Ala His Gln Trp Phe Gly Asp Leu Val Thr Cys Glu Trp Trp Asp Val
        355                 360                 365

Thr Trp Leu Asn Glu Gly Phe Ala Arg Tyr Tyr Gln Tyr Tyr Gly Thr
    370                 375                 380

Ala Leu Val Glu Thr Glu Trp Asp Leu Asp His Gln Phe Val Val Glu
```

-continued

```
            385                 390                 395                 400
        Gln Leu Gln Gly Val Met Gln Met Asp Ser Leu Arg Ser Thr His Pro
                        405                 410                 415
        Met Thr His Pro Val Tyr Thr Gln Ala Gln Thr Ser Gly Ile Phe Asp
                        420                 425                 430
        Asn Ile Ser Tyr Asn Lys Gly Ala Val Met Leu Arg Met Met Glu His
                        435                 440                 445
        Tyr Leu Thr Thr Glu Thr Phe Lys Thr Ala Leu Arg Ala Tyr Ile Lys
                        450                 455                 460
        Asp Arg Ala Phe Lys Thr Thr Arg Pro Glu Asp Leu Phe Asn Ala Leu
        465                 470                 475                 480
        Asn Arg Tyr Asp Pro Asn Ala Arg Ser Tyr Met Glu Pro Trp Thr Val
                        485                 490                 495
        Gln Pro Gly Tyr Pro Leu Val Thr Val Thr Ser His Asp Thr Gly Phe
                        500                 505                 510
        Thr Ile Thr Gln Lys Arg Phe Leu Val Asn Glu Pro Asp His Asn Glu
                        515                 520                 525
        Gln Thr Ala Trp Pro Leu Pro Ile Thr Phe Ala Thr Lys Ala Ser Glu
                        530                 535                 540
        Phe Ser Ile Thr Arg Pro Ala Phe Tyr Thr Gly Met Thr Phe Glu Ile
        545                 550                 555                 560
        Pro Met Gln Gly Ala Ser Asp Val Glu Tyr Phe Ile Leu Asn Asn Gln
                        565                 570                 575
        Gln Val Gly Tyr Tyr Arg Val Asn Tyr Asp Ala Ile Leu Trp Gly Lys
                        580                 585                 590
        Ile Ser Lys Ala Leu His Ser Glu Gly Phe Gly Gly Ile His Val Leu
                        595                 600                 605
        Asn Arg Ala Gln Ile Val Asp Asp Leu Phe Asn Leu Ala Arg Gly Asp
                        610                 615                 620
        Val Val Pro Tyr Gly Thr Ala Leu Glu Ile Leu Glu Tyr Leu Lys Glu
        625                 630                 635                 640
        Glu Thr Glu Tyr Ala Pro Trp Leu Ala Ala Val Asn Gly Leu Thr Thr
                        645                 650                 655
        Leu Ser Arg Arg Ile His Ala Asp Asp Glu Lys Leu Phe Thr Ala His
                        660                 665                 670
        Ile Leu Asp Ile Phe Ser Lys Ala Tyr Asp Ile Val Lys Phe Gln Ala
                        675                 680                 685
        Pro Thr Ala Thr Glu Arg Arg Ile Phe Thr Tyr Met Arg Gln Asn Val
                        690                 695                 700
        Leu Gln Trp Ala Cys Asn Tyr Gly His Glu Glu Cys Ser Lys Ala Ala
        705                 710                 715                 720
        Val Ala Glu Phe His Arg Tyr His Gln Asn Pro Ser Val Lys Val His
                        725                 730                 735
        Pro Asp Leu Arg Gln Val Val Tyr Cys Glu Gly Ile Arg Lys Gly Ser
                        740                 745                 750
        Thr Glu Glu Phe Glu Phe Leu Trp Asn Gln Tyr Leu Thr Thr Asn Val
                        755                 760                 765
        Ala Thr Glu Gln Ile Leu Ile Leu Gln Gly Leu Gly Cys Val Ser Ser
                        770                 775                 780
        Ser Glu Leu Ile Thr Asp Met Leu Asn Gly Ile Ala Ser Pro His Val
        785                 790                 795                 800
        Arg Ser Gln Asp Lys Asn Ala Phe Thr Tyr Val Ile Asn Asn Pro
                        805                 810                 815
```

```
Tyr Thr Leu Pro His Val Ser Arg Tyr Leu Gln Gln Asn His Ala Asn
            820                 825                 830

Trp Ala Ala Ser His Gly Ser Tyr Thr Asn Val Ala Ser Ala Phe Asn
            835                 840                 845

Asn Val Leu Ala Arg Leu Lys Ser Asp Ser Glu Arg Asp Ala Ile Ser
            850                 855                 860

Ala Phe Ile Glu Ser Asn Lys Asn Ile Leu Gly Gln Ala Ala Tyr Asp
865                 870                 875                 880

Ser Ile Lys Ser Gly Leu Glu Asp Tyr Glu Thr Asn Lys Gln Phe Thr
                885                 890                 895

Leu Arg Asn Arg Asp Glu Ile His Glu Phe Leu Asp Asn Lys Ile Asn
            900                 905                 910

Gly Gly Ala Ala Thr Ile Leu Ala Asn Val Ser Met Ile Val Gly Leu
            915                 920                 925

Leu Met Leu Val Leu Ala Arg
    930                 935

<210> SEQ ID NO 3
<211> LENGTH: 28
<212> TYPE: DNA
<213> ORGANISM: Artificial Sequence
<220> FEATURE:
<223> OTHER INFORMATION: Forward primer for cloning AgAPN2ta

<400> SEQUENCE: 3
gtcccatatg tccaccagta tgcaacag                                    28

<210> SEQ ID NO 4
<211> LENGTH: 29
<212> TYPE: DNA
<213> ORGANISM: Artificial Sequence
<220> FEATURE:
<223> OTHER INFORMATION: Reverse primer for cloning AgAPN2ta

<400> SEQUENCE: 4
tactctcgag ccacagaatg gcatcgtag                                   29

<210> SEQ ID NO 5
<211> LENGTH: 29
<212> TYPE: DNA
<213> ORGANISM: Artificial Sequence
<220> FEATURE:
<223> OTHER INFORMATION: Forward primer for cloning AgAPN2tb

<400> SEQUENCE: 5
cattcatatg ggaaaaatca gcaaggcgc                                   29

<210> SEQ ID NO 6
<211> LENGTH: 26
<212> TYPE: DNA
<213> ORGANISM: Artificial Sequence
<220> FEATURE:
<223> OTHER INFORMATION: Reverse primer for cloning AgAPN2tb

<400> SEQUENCE: 6
aggcctcgag cacattcgtg taacta                                      26

<210> SEQ ID NO 7
<211> LENGTH: 33
<212> TYPE: DNA
<213> ORGANISM: Artificial Sequence
<220> FEATURE:
```

<223> OTHER INFORMATION: Forward primer for cloning AgAPN2ta deletion 1

<400> SEQUENCE: 7
gactcatatg gtctacacgc aagctcagac cag                33

<210> SEQ ID NO 8
<211> LENGTH: 34
<212> TYPE: DNA
<213> ORGANISM: Artificial Sequence
<220> FEATURE:
<223> OTHER INFORMATION: Forward primer for cloning AgAPN2ta deletion 2

<400> SEQUENCE: 8
ggtcgaattc accagccacg acactggatt cacc                34

<210> SEQ ID NO 9
<211> LENGTH: 33
<212> TYPE: DNA
<213> ORGANISM: Artificial Sequence
<220> FEATURE:
<223> OTHER INFORMATION: Reverse primer for cloning AgAPN2ta deletion 2

<400> SEQUENCE: 9
gcgtgaattc gggatgagtc atagggtggg tag                33

<210> SEQ ID NO 10
<211> LENGTH: 32
<212> TYPE: DNA
<213> ORGANISM: Artificial Sequence
<220> FEATURE:
<223> OTHER INFORMATION: Forward primer for cloning AgAPN2ta deletion 3

<400> SEQUENCE: 10
cattgaattc ctcgagcacc accaccacca cc                32

<210> SEQ ID NO 11
<211> LENGTH: 34
<212> TYPE: DNA
<213> ORGANISM: Artificial Sequence
<220> FEATURE:
<223> OTHER INFORMATION: Reverse primer for cloning AgAPN2ta deletion 3

<400> SEQUENCE: 11
cgtggaattc aacagtgacc agaggatagc cagg                34

<210> SEQ ID NO 12
<211> LENGTH: 34
<212> TYPE: DNA
<213> ORGANISM: Artificial Sequence
<220> FEATURE:
<223> OTHER INFORMATION: Forward primer for cloning AgAPN2tb deletion 1

<400> SEQUENCE: 12
tcgccatatg catgctgatg atgagaagct gttc                34

<210> SEQ ID NO 13
<211> LENGTH: 36
<212> TYPE: DNA
<213> ORGANISM: Artificial Sequence
<220> FEATURE:
<223> OTHER INFORMATION: Forward primer for cloning AgAPN2tb deletion 2

<400> SEQUENCE: 13
gttcaagctt aatcaatatc tgacaacgaa cgtggc                36

```
<210> SEQ ID NO 14
<211> LENGTH: 33
<212> TYPE: DNA
<213> ORGANISM: Artificial Sequence
<220> FEATURE:
<223> OTHER INFORMATION: Reverse primer for cloning AgAPN2tb deletion 2

<400> SEQUENCE: 14
tggaaagctt gtctaggatg tgggccgtga aca                                 33

<210> SEQ ID NO 15
<211> LENGTH: 34
<212> TYPE: DNA
<213> ORGANISM: Artificial Sequence
<220> FEATURE:
<223> OTHER INFORMATION: Reverse primer for cloning AgAPN2tb deletion 3

<400> SEQUENCE: 15
gatactcgag ccacaagaac tcgaactcct ccgt                                34
```

NON-CADHERIN POLYPEPTIDE POTENTITATORS OF CRY PROTEINS

CROSS-REFERENCE TO RELATED APPLICATION

The subject application claims priority to U.S. provisional application Ser. No. 61/325,944, filed Apr. 20, 2010.

STATEMENT REGARDING FEDERALLY SPONSORED RESEARCH

This invention was made with government support under National Institutes of Health Grant R01 AI 29092. The U.S. Government has certain rights in this invention.

BACKGROUND

The bacterium *Bacillus thuringiensis israelensis* (Bti) has been used worldwide as an important mosquito control agent for decades (Lacey, 2007). The active ingredient of Bti is a parasporal crystal complex composed of four Cry proteins (Cry4Aa, Cry4Ba, Cry10Aa and Cry11Aa) and two cytolytic proteins (Cyt1Aa and Cyt2Ba) (Porter et al., 1993). Concerns about potential mosquito resistance development to Bti have led to discoveries of other mosquitocidal toxins with high potency. Cry11Ba produced by B.t. *jegathesan* (Btjeg) is the single most effective toxin against mosquitoes to date. Cry11Ba shares 58% similarity to Cry11Aa and is 7- to 34-fold more toxic to mosquito larvae than the related Cry11Aa (Delécluse et al., 1995).

The resolved structures of Cry proteins show a conservative 3D-topology, suggesting a common mode-of-action. (Boonserm et al., 2005; Boonserm et al., 2006; Galitsky et al., 2001; Grochulski et al., 1995; Li et al., 1991; Morse et al., 2001). Two models regarding the intoxication process of toxins are proposed [reviewed in (Pigott and Ellar, 2007)]. The colloid-osmotic lysis model suggests that proteolytically activated toxins bind cadherin, oligomerize and then bind glycosylphosphatidylinositol (GPI)-anchored aminopeptidase (APN) and GPI-anchored alkaline phosphatase (ALP) to induce toxicity (Bravo et al., 2004). An alternative model proposes the activation of intracellular signaling pathways by toxin monomer binding to cadherin without the need of the toxin oligomerization step to cause cell death (Zhang et al., 2006). Whether toxicity is independent of toxin oligomerization remains arguable, the toxin-receptor interaction has been elucidated in both models as the major determinant of toxin specificity.

APN has long been implicated as a Cry1 toxin binding protein in a number of lepidopteran species [reviewed in (Pigott and Ellar, 2007)]. As a glycoprotein, APN interacts with Cry toxins through either glycan moieties or amino acid residues. For example, Cry1Ac has been shown to bind an N-acetylgalactosamine (GalNAc) moiety on APNs from *Manduca sexta* (Burton et al., 1999), *Heliothis virescens* (Luo et al., 1997) and *Lymantria dispar* (Valaitis et al., 1997). In contrast, Cry1Aa and Cry1Ab are believed to bind APN only in a carbohydrate-independent manner (Masson et al., 1995; Nakanishi et al., 2002). Yaoi et al. (1999) localized a Cry1Aa binding site on *Bombyx mori* APN to the region between $^{135}$Ile and $^{198}$Pro. This region contains amino acid residues RXXFPXXDEP conserved among APNs from different species, and thus has been suggested as a common Cry1Aa binding region (Nakanishi et al., 2002; Nakanishi et al., 1999). Recently, a 112-kDa APN (AaeAPN1) in *Aedes aegypti* has been identified to bind Cry11Aa through the region between $^{525}$Arg and $^{778}$Leu. (Chen et al., 2009). Unlike the Cry1Aa binding site near the N-terminus, The Cry11Aa binding region was located to the C-terminal region of AaeAPN1. In our previous study, we identified a 106-kDa APN (AgAPN2) as a Cry11Ba binding protein and putative receptor in An. *gambiae* (Zhang et al., 2008). The 70-kDa partial AgAPN2 expressed in *E. coli* binds Cry11Ba with high affinity and blocks Cry11Ba toxicity towards mosquito larvae. This APN fragment shows no similarity to the Cry1Aa binding site. Collectively, the data provide evidence that a few primary amino acid sequences on APNs are probably key factor in determining toxin specificities.

To further characterize interactions between Cry11Ba and 70-kDa AgAPN2t we divided the peptide into two fragments of similar size. We showed that one fragment inherited the inhibitory effect of the 70-kDa peptide. By using a combination of in-frame deletions and binding assays, we located a region ($^{336}$S-P$^{420}$) on AgAPN2 that is essential for toxin binding and blocking toxicity. Unexpectedly, we also observed an enhancing effect of another fragment ($^{591}$G-V$^{843}$) on Cry11Ba toxicity. This is the first report that a non-cadherin fragment of a Cry toxin-binding protein can act as a synergist of Cry toxicity to pest insects (Chen et al., 2007; Park et al., 2009a; Park et al., 2009b).

BRIEF SUMMARY

The subject invention relates in part to fragments of non-cadherin Cry toxin binding proteins, wherein the fragments potentiate, or act as synergists with, the insecticidal activity of Cry proteins. In some preferred embodiments, the binding protein (a Cry protein receptor on insect midgut cells) is an aminopeptidase. In preferred embodiments, the fragment comprises a Cry protein binding region.

BRIEF DESCRIPTION OF THE FIGURES

FIG. 1(A) Schematic representation of the truncations of AgAPN2. FIG. 1(B). SDS-PAGE of purified AgAPN2ta and -2tb. FIG. 1(C) Far-UV CD spectrum (190-240 nm) of AgAPN2ta peptide. FIG. 1(D) Far-UV CD spectrum (190-240 nm) of AgAPN2tb peptide.

FIG. 2: AgAPN2ta inhibits and AgAPN2tb enhances Cry11Ba toxicity to An. *gambiae* larvae. Soluble Cry11Ba alone or with APN inclusions at a toxin/peptide molar ratio of 1:100 were diluted in plastic plates containing 2 ml of deionized water and tested against ten early 4$^{th}$ instar larvae of An. *gambiae*. Each treatment was in triplicate and the bioassays were conducted three times. Larval mortality was recorded after 24 h. FIG. 2(A) Mean percent mortality (±SE) of larval mosquitoes treated with 0.5 µg/ml Cry11Ba when APN inclusion bodies were absent or present. FIG. 2(B) Mean percent mortality (±SE) of larval mosquitoes treated with 4 µg/ml Cry11Ba when APN inclusion bodies were absent or present. An asterisk indicates a significant difference between larval mortality with Cry11Ba treatment alone and that with Cry11Ba plus peptide treatment at the same toxin dose (one-way ANOVA, P<0.001).

(FIG. 3C and FIG. 3D) Shared bindings of AgAPN2ta and AgAPN2tb to Cry11Ba were determined by competitive binding assays using 20 nM biotinylated AgAPN2ta or -2tb peptides as probes with increasing concentrations of nonlabeled homologous or heterologous peptides.

FIG. 4: A 10-kDa segment deletion in the N-terminus causes AgAPN2ta loss of inhibitory effect to Cry11Ba toxicity. FIG. 4(A) Schematic representation of the construction of in-frame deletions of AgAPN2ta. FIG. 4(B) Partially purified recombinant AgAPN2ta and its deletions were resolved by SDS-PAGE and stained with Coomassie blue. FIG. 4(C) Mean percent mortality (±SE) of larval mosquitoes treated with 4 μg/ml Cry11Ba when APN inclusion bodies were absent or present. An asterisk indicates a significant difference between larval mortality with Cry11Ba treatment alone and that with Cry11Ba plus peptide treatment at the same toxin dose (one-way ANOVA, P<0.001).

FIG. 5(A) AgAPN2ta/Del1 partially compete the binding of AgAPN2ta to Cry11Ba in competition binding assays. Microtiter plates coated with 1 μg trypsinized Cry11Ba were incubated with 20 nM biotinylated AgAPN2ta protein and increasing concentrations of unlabeled AgAPN2ta or AgAPN2ta derivatives. FIG. 5(B) AgAPN2ta derivatives compete the binding of AgAPN2ta to Cry11Ba in saturation binding assays. Microplates coated with 1 μg of trypsinized Cry11Ba were incubated with increasing nanomolar concentrations of biotinylated AgAPN2ta peptide alone or with a 1000-fold molar excess of unlabeled peptides. FIG. 5(C) Average (±SE) binding of 2.5 nM of $^{125}$I-Cry11Ba to 8 μg An. gambiae BBMV in the presence or absence of 10 μM of competitors. Different letters above the error bars indicate significant differences between means.

FIG. 6(A) Schematic representation of the construction of in-frame deletions of AgAPN2tb. FIG. 6(B) Partially purified recombinant AgAPN2tb and its deletions were resolved by SDS-PAGE and stained with Coomassie blue. FIG. 6(C) Mean percent mortality (±SE) of larval mosquitoes treated with 0.5 μg/ml Cry11Ba when APN inclusion bodies were absent or present. An asterisk indicates a significant difference between larval mortality with Cry11Ba treatment alone and that with Cry11Ba plus peptide treatment at the same toxin dose (one-way ANOVA, P<0.001).

FIG. 7(A) AgAPN2tb derivatives compete AgAPN2tb binding to Cry11Ba in competition binding assays. Microtiter plates coated with 1 μg trypsinized Cry11Ba were incubated with 20 nM biotinylated AgAPN2ta protein and increasing concentrations of unlabeled AgAPN2tb or AgAPN2tb derivatives. FIG. 7(B) AgAPN2tb derivatives compete the binding of AgAPN2tb to Cry11Ba in saturation binding assays. Microplates coated with 1 μg of trypsinized Cry11Ba were incubated with increasing nanomolar concentrations of biotinylated AgAPN2tb peptide alone or with a 1000-fold molar excess of unlabeled peptides. FIG. 7(C) Average (±SE) binding of 2.5 nM of $^{125}$I-Cry11Ba to 8 μg An. gambiae BBMV in the presence or absence of 10 μM of competitors. Different letters above the error bars indicate significant differences between means.

DETAILED DESCRIPTION

Figure 1:
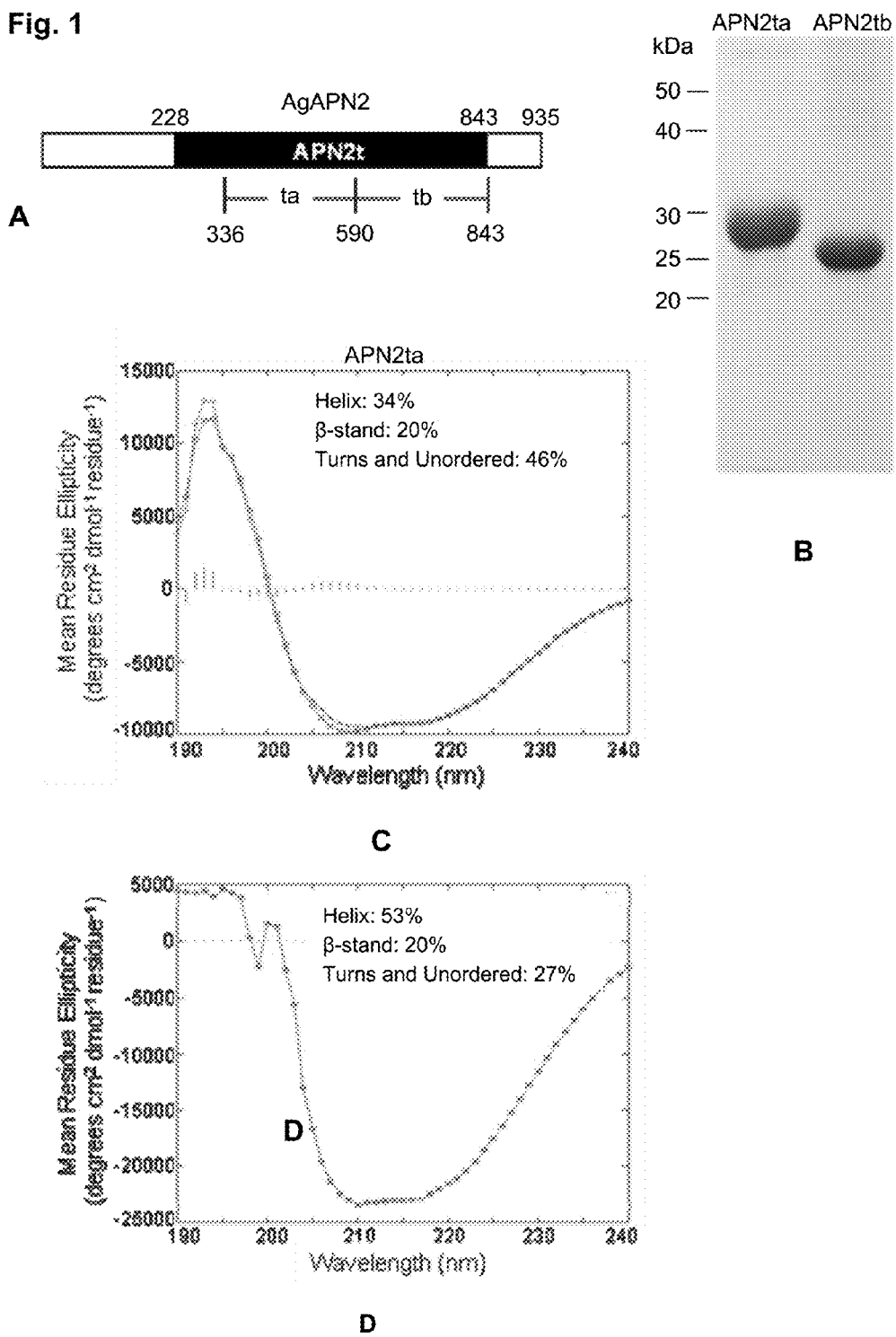
FIG. 1: Purified AgAPN2ta and -2tb fragments demonstrate partially folded structure.

The subject invention relates in part to fragments of non-cadherin Cry toxin binding proteins, wherein the fragments potentiate, or act as synergists with, the insecticidal activity of Cry proteins. In some preferred embodiments, the binding protein (a Cry protein receptor on insect midgut cells) is an aminopeptidase. In preferred embodiments, the fragment comprises a Cry protein binding region.

It is known in the art that sequences for Bacillus thruingiensis (B.t.) Cry proteins, and source isolates, are available in GENBANK and are listed on the Crickmore et al. website (lifesci.sussex.ac.uk/home/Neil_Crickmore/Bt/intro.html.)

B.t. Cry nomenclature is relatively standardized. As used in the art and herein, boundaries are drawn at approximately 95% (Cry11Ba's), 78% (Cry11B's), and 45% (Cry11's) sequence identity, per "Revision of the Nomenclature for the Bacillus thuringiensis Pesticidal Crystal Proteins," N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813. Mosquitocidal Cry proteins for use according to the subject invention include Cry19s, Cry1Cs, and Cry4s.

An "isolated" protein, polypeptide, or polynucleotide is a non-naturally occurring molecule, or a molecule in a non-naturally occurring state, such as in purified form in a man-made composition. An isolated polynucleotide can also be under the control of, or operably linked to, a heterologous promoter—of an origin that is not naturally associated with the isolated polynucleotide. A non-native promoter could be a non-bacterial promoter associated with a polynucleotide derived from a bacterium, or a non-insect promoter associated with an insect-derived gene. Non-naturally occurring (expression) constructs are included.

Cry11Ba produced by Bacillus thuringiensis jegathesan is an active toxin against mosquito Anopheles gambiae. See also SEQ ID NO:1. A 106-kDa aminopeptidase N, called AgAPN2 (SEQ ID NO:2), was previously identified as a Cry11Ba receptor in An. gambiae. A 70-kDa fragment of AgAPN2 expressed in Escherichia coli binds Cry11Ba with high affinity ($K_d$=6.4 nM) and inhibits Cry11Ba activity by 98% in bioassays [Zhang et al. (2008) Biochemistry 47, 11263-72]. To identify regions involved in effecting toxicity, we truncated the 70-kDa APN fragment into peptides of 28- and 30-kDa and tested their abilities to mediate toxicity and bind Cry11Ba. While AgAPN2ta reduced Cry11Ba toxicity by 85%, AgAPN2tb showed a significant enhancement effect on Cry11Ba toxicity. The purified peptides showed evidence of structural folding and bound the same site(s) on Cry11Ba with high affinity. The inhibitory AgAPN2ta blocked Cry11Ba binding to brush border membrane vesicles (BBMV) of An. gambiae whereas the toxicity enhancing AgAPN2tb increased Cry11Ba binding on BBMV. A deletion at the N-terminus ($^{336}$S P$^{420}$) of AgAPN2ta significantly reduced AgAPN2ta binding to Cry11Ba and its inhibitory effect. Deletion of the central region ($^{676}$I-W$^{760}$) of AgAPN2tb resulted in AgAPN2tb loss of increased toxin binding and toxicity enhancement effect but no change in Cry11Ba binding. A 'bridge' model is proposed for AgAPN2tb action whereby the peptide binds Cry11Ba and vectors the Cry11Ba to sites on the larval midgut.

Figure 4:
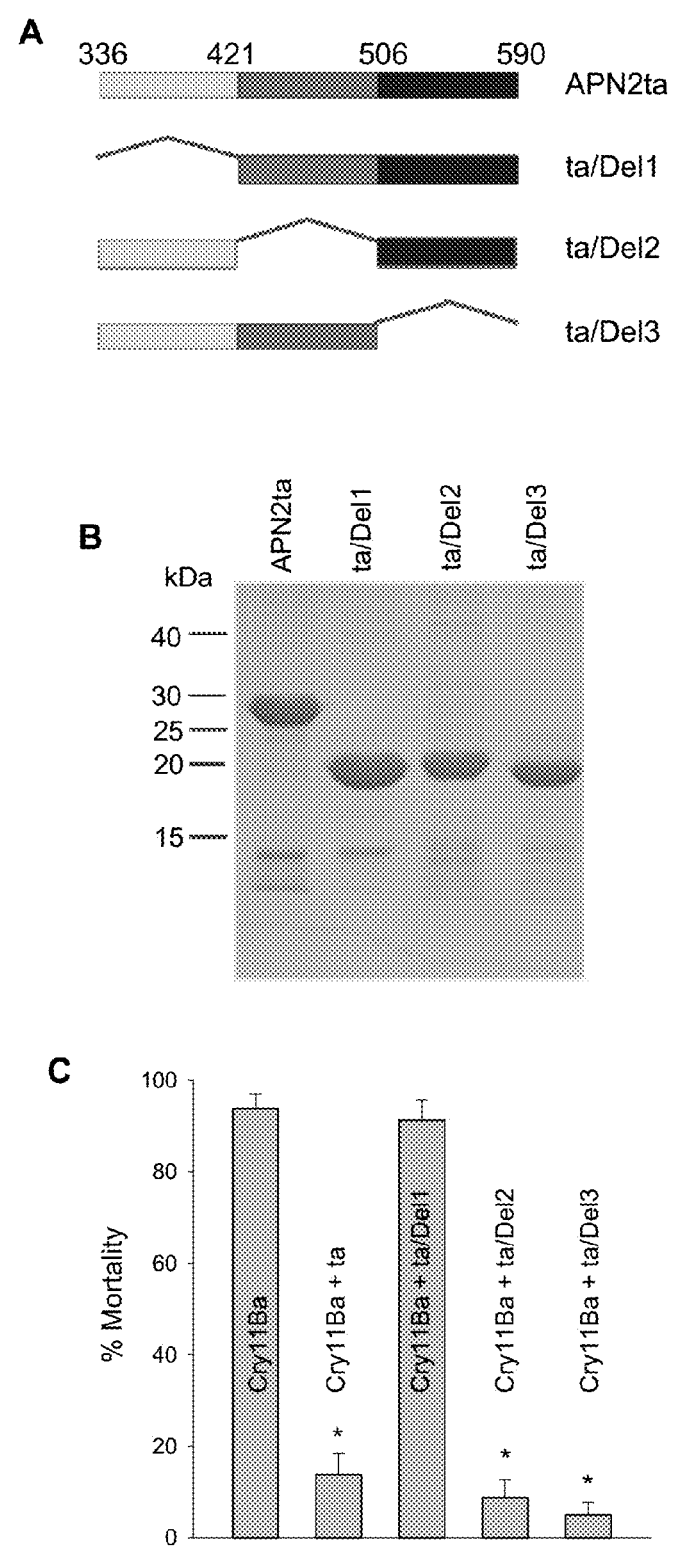
Figure 5:
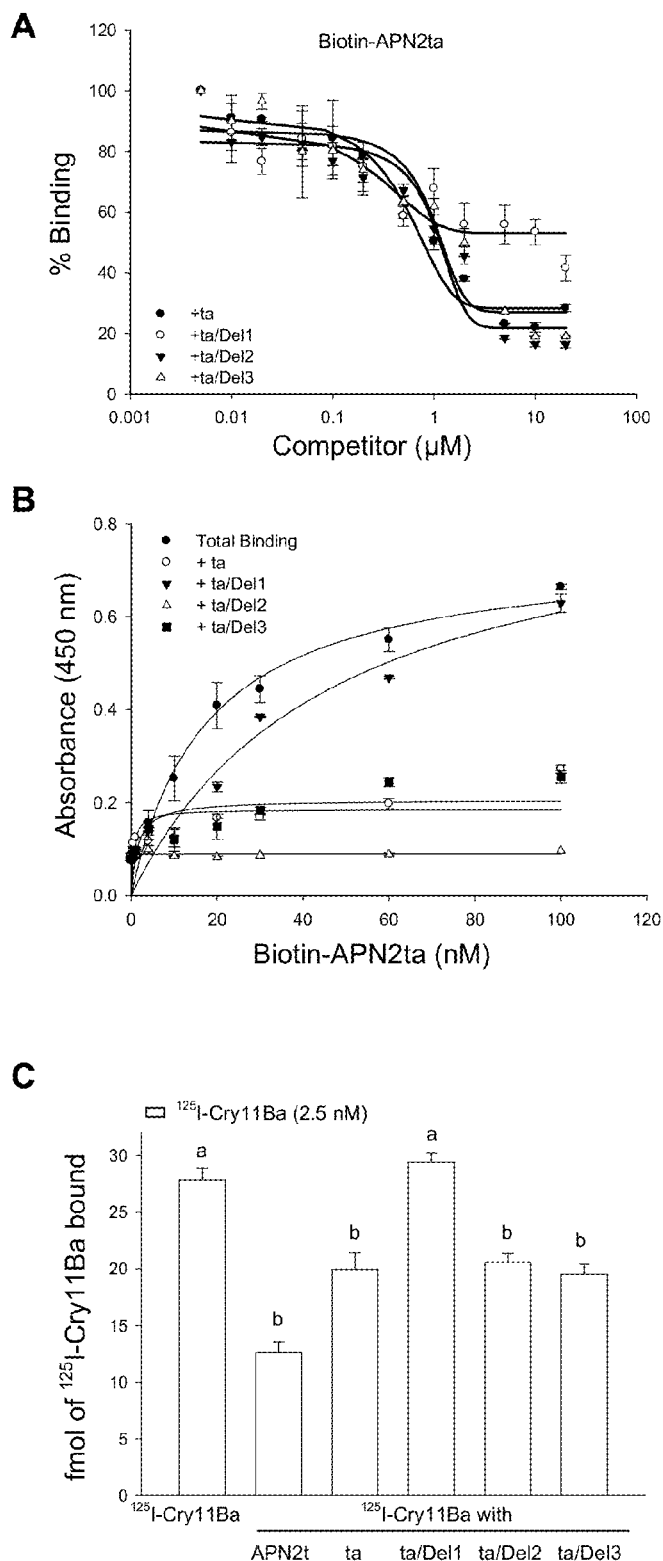
FIG. 5: Analysis of the interaction of AgAPN2ta and its deletions to Cry11Ba.

In this work, we identified two fragments of the Cry11Ba binding protein AgAPN2 that bind toxin yet have opposite effects on Cry11Ba binding to BBMV and toxicity to larvae. The 30-kDa AgAPN2ta peptide retains the inhibitory effect of 70-kDa AgAPN2t peptide. AgAPN2ta binds Cry11Ba with high affinity ($K_d$=16.7 nM), an affinity comparable to the binding of the parental AgAPN2t peptide ($K_d$=6.4 nM). Using a scanning-block deletion method, we localized the Cry11Ba binding site between $^{336}$Ser and $^{420}$Pro. The AgAPN2ta/Del1 peptide without this region loses the ability to inhibit Cry11Ba binding to BBMV and neutralize toxicity to larvae (FIGS. 4 and 5). Our data support the conclusion that the $^{336}$Ser to $^{420}$Pro region of AgAPN2 contains a binding epitope that is involved in Cry11Ba interaction with AgAPN2 and possibly other Cry11Ba binding molecules on the larval brush border. This 85-amino-acid region shows no sequence similarity to the reported Cry1A binding site on *B. mori* APN and the Cry11Aa binding area on *A. aegypti* APN (Chen et al., 2009; Nakanishi et al., 1999) suggesting that an amino acid primary structure in this region may play an important role in recognition by Cry11Ba toxin and may be a determinant of Cry11Ba larval specificity.

We unexpectedly discovered that the C-terminal region of AgAPN2t synergized Cry11Ba toxicity in bioassays with mixtures of Cry11Ba and AgAPN2tb inclusions. A similar in vivo approach led to the discovery of the CR12-MPED fragment from *M. sexta* cadherin Bt-R1 as a synergist of Cry1A toxicity to lepidopteran larvae (Chen et al., 2007). In the case of the CR12-MPED peptide, the synergism requires the Cry1Ab-binding epitope. Removal of the eight-amino-acid binding epitope on CR12-MPED resulted in loss of binding to Cry1A and its synergistic ability.

Figure 6:
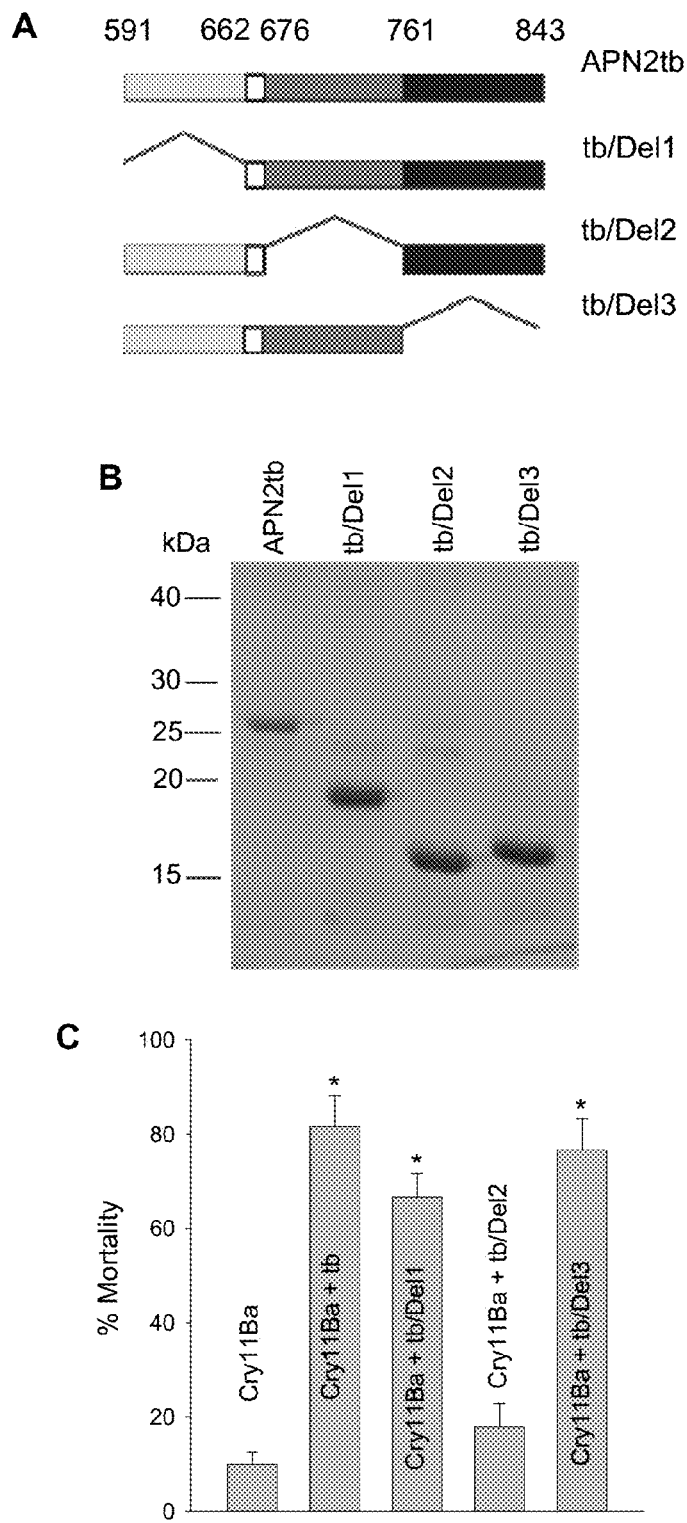
FIG. 6: A deletion of eighty-five amino acids in the central region causes AgAPN2tb loss of enhancement effect to Cry11Ba toxicity.
Figure 7:
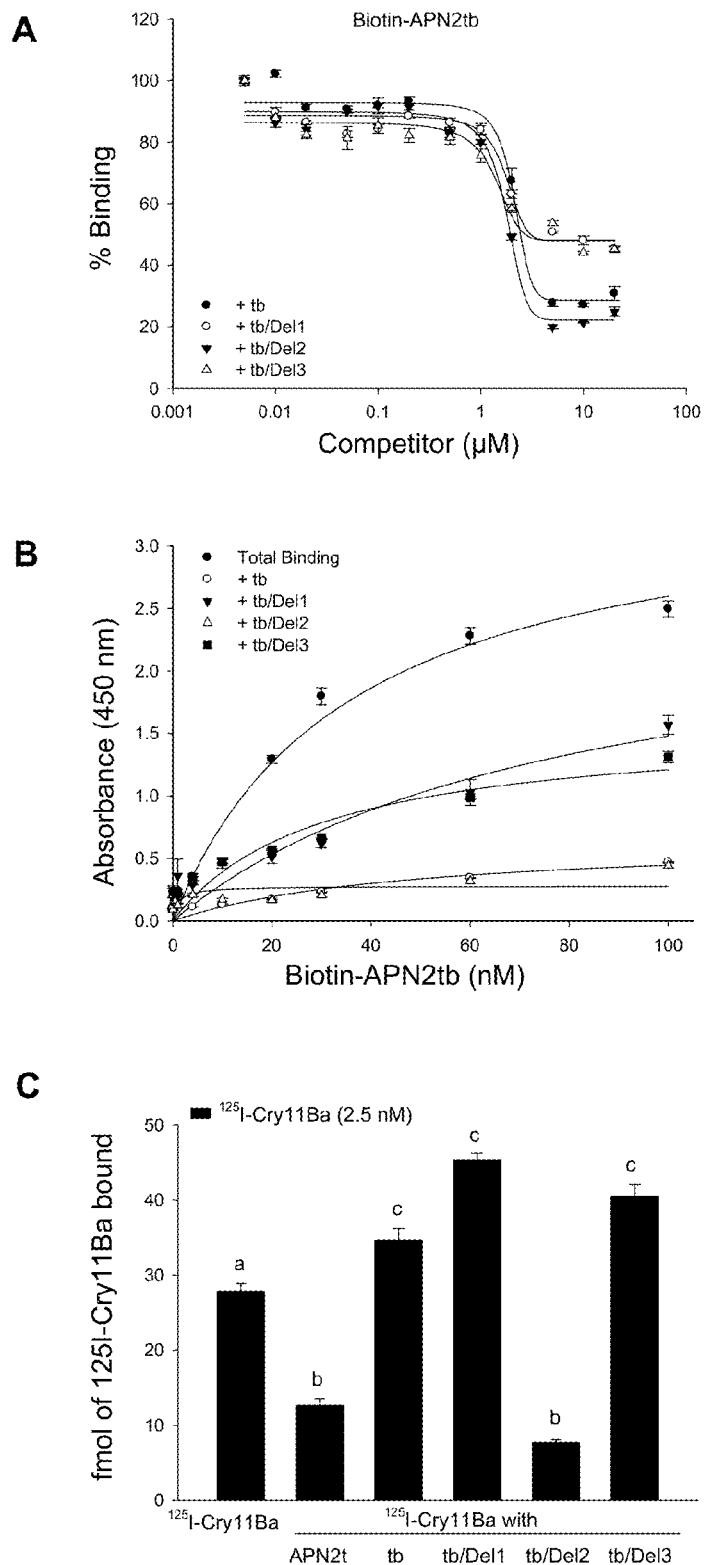
FIG. 7: AgAPN2tb/Del2 loses the ability to enhance Cry11Ba toxicity while still binds to Cry11Ba.

In our experiments, we showed that AgAPN2tb bound Cry11Ba with nM affinity ($K_d$=26.4 nM) (FIG. 3B), a value comparable to the high-affinity binding of Cry1Ab to cadherin peptide CR12-MPED ($K_d$=9.17 nM). Thus, we hypothesized that the lack of insecticidal synergy by AgAPN2tb/Del2 peptide would correlate with loss of a Cry11Ba binding site. However, AgAPN2tb/Del2 was proved to be an effective competitor of AgAPN2tb binding to Cry11Ba in both competition and saturation ELISA binding assays (FIGS. 6 and 7). In contrast, the AgAPN2tb/Del1 and -2tb/Del3 synergistic peptides each had a deleted Cry11Ba binding site which resulted in the ability to compete only 50% of the biotin-AgAPN2tb bound to Cry11Ba (FIG. 7A and FIG. 7B). Rather than affecting peptide binding to Cry11Ba deletion of the middle region of AgAPN2tb, as in AgAPN2tb/Del2 peptide, resulted in loss of enhanced $^{125}$I-Cry11Ba binding to BBMV. Synergism of Cry11Ba binding and toxicity by a derivative of AgAPN2tb appears to require the middle Del2 region and either the N- or C-terminal regions of AgAPN2tb.

One explanation of the observed synergism is that the fragment being deleted in AgAPN2tb/Del2 could act as a "bridge" to vector toxins to receptors on the midgut brush border. The concept of bridge was proposed to account for CR12-MPED synergizing Cry1Ab toxicity, whereby CR12-MPED binding to BBMV increases the probability of toxin interaction with Cry1A receptors (Chen et al., 2007). However, it is important to notice that CR12-MPED binds *M. sexta* BBMV with high affinity (32 nM), whereas AgAPN2tb and its derivatives only bind An. *gambiae* BBMV in an unsaturable manner (data not shown).

An alternative explanation for toxicity enhancement is that AgAPN2tb could modify interactions between Cry11Ba and receptor molecules on epithelial cells of mosquito midgut. Studies with *M. sexta* synergist CR12-MPED have shown that it is able to promote toxin oligomerization, an essential step for Cry1A activity in the pore-formation model (Pacheco et al., 2009b; Soberón et al., 2007). A *Helicoverpa armigera* cadherin fragment was also reported to facilitate oligomer formation and enhance Cry1Ac toxicity (Peng et al., 2010). However, no significant Cry11Ba oligomerization was observed with the addition of AgAPN2tb in the presence of trypsin and BBMV (data not shown). We cannot exclude the possibility that AgAPN2tb is involved indirectly in the modification of toxin conformation.

Recently, an updated pore-formation model proposes that depending on the oligomeric state of the toxin, Cry1A binds cadherin and APN in a sequential "ping pong" fashion (Pacheco et al., 2009a). Therefore, different interaction of toxin with two proteins may implicate different mechanisms of synergism for APN and cadherin proteins. In addition, BBMV binding assays in this study identified that the peptides capable of enhancing Cry11Ba toxicity could also increase Cry11Ba binding to BBMV (FIG. 7C). On the contrary, a cadherin fragment was found to synergize mosquitocidal Cry4Ba toxicity but inhibits toxin binding to BBMV (Park et al., 2009b). If these initial observations are further validated, it may add additional complexity to the synergistic mechanisms in mosquitoes.

In this research, we have empirically determined that two fragments of AgAPN2 bound Cry11Ba with high affinity. Competitive binding assays using two APN fragments as homologous or heterologous competitors indicated that the two APN fragments share the same binding site(s) on Cry11Ba. It is possible that Cry11Ba bind multiple sites on AgAPN2. *Manduca* APN and *Heliothis* APN are reported to bind Cry1A with 2:1 toxin-receptor stoichiometries (Luo et al., 1997; Masson et al., 1995). Although speculative, it is possible that Cry11Ba binds sequentially to two sites on AgAPN2 in a 1:1 toxin-receptor ratio, as described for the interaction between Cry1Ac and *Lymantria dispar* APN, whereby Cry1Ac binding to site 1 initiates a fast reversible interaction with the receptor that is followed by a high-affinity binding to site 2 (Jenkins et al., 2000). The authors proposed that Cry toxin undergoes a conformational change upon binding to APN site 2 that leads to an irreversible insertion into the target membrane. It remains to be determined how toxin binding to receptor triggers the event. Our work has localized the Cry11Ba binding regions on AgAPN2. We have also identified a non-toxin binding region on AgAPN2 that is crucial for the enhancement of Cry11Ba toxicity. It is conceivable that this fragment may be involved in initiation of toxin conformational change necessary for insertion. Further investigation of the interaction between Cry11Ba and these two regions on AgAPN2 will help to better understand the mechanism of toxin pore-formation on the cell membrane.

EXAMPLES

Example 1

Purification and Biotinylation of Cry11Ba Toxin

The Bt strain 407 (Delécluse et al., 1995) producing Cry11Ba protein was grown in complex sporulation medium (Zhang et al., 2008) supplemented with erythromycin antibiotic. The spore crystal mixture was washed, crystals separated on NaBr step gradients and protoxin prepared as previously described (Zhang et al., 2008). Cry11Ba protoxin was activated with bovine pancreatic trypsin (Sigma) at a ratio of 10:1 in mass ratio (protoxin:trypsin) for 2 h at 37° C. Activated Cry11Ba was purified by fast protein liquid chromatography (FPLC), using a Bio-Scale™ mini High Q cartridge (Bio-Rad, Richmond, Calif.).

Example 2

Cloning and Expression of APN Fragments

Two pairs of specific primers listed in Table 1 were designed according to the sequence of AgAPN2 (GenBank accession number EU827528).

TABLE 1

Primers used in this study
(endonuclease sites were underlined)

| Primer | Primer Sequence (5'-3') |
|---|---|
| Primers for cloning AgAPN2ta and AgAPN2tb | |
| AgAPN2ta-F | 5'-GTCC<u>CATATG</u>TCCACCAGTATGCAACAG-3' (SEQ ID NO: 3) |
| AgAPN2ta-R | 5'-TACT<u>CTCGAG</u>CCACAGAATGGCATCGTAG-3' (SEQ ID NO: 4) |
| AgAPN2tb-F | 5'-CATT<u>CATATG</u>GGAAAAATCAGCAAGGCGC-3' (SEQ ID NO: 5) |
| AgAPN2tb-R | 5'-AGGC<u>CTCGAG</u>CACATTCGTGTAACTA-3' (SEQ ID NO: 6) |
| Primers for cloning AgAPN2ta deletions | |
| AgAPN2ta-Del1 | |
| AgAPN2ta/Del1-F | 5'-GACT<u>CATATG</u>GTCTACACGCAAGCTCAGACCAG-3' (SEQ ID NO: 7) |
| AgAPN2ta-R | 5'-TACT<u>CTCGAG</u>CCACAGAATGGCATCGTAG-3' (SEQ ID NO: 4) |
| AgAPN2ta-Del2 | |
| AgAPN2ta/Del2-F | 5'-GGTC<u>GAATTC</u>ACCAGCCACGACACTGGATTCACC-3' (SEQ ID NO: 8) |
| AgAPN2ta/Del2-R | 5'-GCGT<u>GAATTC</u>GGGATGAGTCATAGGGTGGGTAG-3' (SEQ ID NO: 9) |
| AgAPN2ta-Del3 | |
| AgAPN2ta/Del3-F | 5'-CATT<u>GAATTC</u>CTCGAGCACCACCACCACCACC-3' (SEQ ID NO: 10) |
| AgAPN2ta/Del3-R | 5'-CGTG<u>GAATTC</u>AACAGTGACCAGAGGATAGCCAGG-3' (SEQ ID NO: 11) |
| Primers for cloning AgAPN2tb deletions | |
| AgAPN2tb-Del1 | |
| AgAPN2tb/Del1-F | 5'-TCGC<u>CATATG</u>CATGCTGATGATGAGAAGCTGTTC-3' (SEQ ID NO: 12) |
| AgAPN2tb-R | 5'-AGGC<u>CTCGAG</u>CACATTCGTGTAACTA-3' (SEQ ID NO: 6) |
| AgAPN2tb-Del2 | |
| AgAPN2tb/Del2-F | 5'-GTTC<u>AAGCTT</u>AATCAATATCTGACAACGAACGTGGC-3' (SEQ ID NO: 13) |
| AgAPN2tb/Del2-R | 5'-TGGA<u>AAGCTT</u>GTCTAGGATGTGGGCCGTGAACA-3' (SEQ ID NO: 14) |
| AgAPN2tb-Del3 | |
| AgAPN2tb-F | 5'-CATT<u>CATATG</u>GGAAAAATCAGCAAGGCGC-3' (SEQ ID NO: 5) |
| AgAPN2tb/Del3-R | 5'-GATA<u>CTCGAG</u>CCACAAGAACTCGAACTCCTCCGT-3' (SEQ ID NO: 15) |

PCR amplifications were performed using pGEM-AgAPN2 (Zhang et al., 2008) as template with 30 cycles of 94° C. for 30 sec, 58° C. for 30 sec, and 72° C. for 1 min. The resulting PCR fragments were cloned into the protein expression vector pET-30a (+) (Novagen, Madison, Wis.) through NdeI/XhoI cuts to yield plasmids pET-AgAPN2ta and pET-AgAPN2tb, respectively. The coding sequences were confirmed by sequencing. The pET-constructs were transformed into *E. coli* strain BL21-CodonPlus (DE3)/pRIL (Stratagene, La Jolla, Calif.). The APN peptides were overexpressed in *E. coli* as inclusion bodies which were stored at 5° C. in deionized water until needed. The protein components of inclusion bodies were examined by 12% SDS-PAGE and Coomassie blue G-250 staining. For the following binding assays, inclusion bodies were centrifuged and solubilized in 8M urea, 20 mM $Na_2CO_3$, pH 9.6. Soluble AgAPN peptides were purified by a HiTrap Ni2+-chelating HP column (GE Healthcare, Piscataway, N.J.) according to manufacturer's manual and dialyzed against 10 mM $Na_2CO_3$, pH 9.6.

Example 3

Circular Dichroism (CD) Spectroscopy

Inclusion bodies of AgAPN2ta and AgAPN2tb were solubilized in 8M urea, 20 mM $Na_2HPO_4$, 0.5 M NaCl, pH 7.6 and proteins purified by a HiTrap $Ni^{2+}$-chelating HP column (GE Healthcare, Piscataway, N.J.) according to the manufacturer's manual. Purified AgAPN2ta and AgAPN2tb peptides were dialyzed in 10 mM $Na_2CO_3$, pH 9.6, at a concentration of 10 μM. CD spectroscopy measurement was performed according to (Chen et al., 2007). The acquired CD spectra were analyzed by CDSSTR algorithms (Lobley et al., 2002; Whitmore and Wallace, 2004, 2008) on DICHROWEB (see website at dichroweb.cryst.bbk.ac.uk/html/home.shtml).

Example 4

In-Frame Deletion of AgAPN2ta and AgAPN2tb

Specific primers for cloning AgAPN2ta/Del1 and AgAPN2tb/Del1 were designed and listed in Table 1. PCR amplifications and transformations were performed as described in 2.2. The strategy for constructing other in-frame deletions was based on the Stratagene QuickChange method described previously (Chen et al., 2007; Hua et al., 2004). Briefly, 5'- and 3' primer pairs were designed that were complementary to the region to be deleted and have an endonuclease cleavage site at each end (Table 1). PCR was performed using Elongase Enzyme Mix (Invitrogen, Carlsbad, Calif.) with pET-AgAPN2ta or pET-AgAPN2tb plasmid as template. The PCR product was gel-purified, digested with DpnI and the corresponding endonuclease, and then transformed into *E. coli* BL21 after ligation. The coding regions of all mutated plasmids were sequenced. Culture growth, protein induction and purification of expressed peptides are described in 2.2. The expressed AgAPN2 peptides have a stretch of contiguous amino acid residues deleted that were replaced with E and F or K and L due to the introduction of EcoRI or HindIII site in the DNA sequence.

Example 5

Mosquito Bioassays

The colony of *Anopheles gambiae* (CDC G3 strain) was maintained as described previously (Zhang et al., 2008). Soluble Cry11Ba was mixed with APN inclusion bodies at 1:100 toxin:peptide molar ratio. Cry11Ba alone or toxin-peptide mixtures was transferred to wells of a 6-well Costar culture plate (Corning). Ten early $4^{th}$ instar larvae were added to each well and the plates incubated at 27° C. Each treatment was in triplicate and the bioassays were conducted at least three times, and there was a control of inclusion bodies alone. Larval mortality was recorded after 24 h.

Example 6

Microtiter Binding Assays

The biotinylation and dialysis of APN peptides were described previously (Zhang et al., 2008). Microtiter plates (high binding 96-well, Immulon® 2HB, Thermo Fisher Scientific Inc., Waltham, Mass.) were coated overnight at 4° C. with 1.0 µg Cry11Ba/well in 100 µl coating buffer (100 mM Na$_2$CO$_3$, pH 9.6) and blocked as described in (Zhang et al., 2008). In a saturation binding assay, biotinylated AgAPN2 peptides were diluted to the desired concentrations (0.5 nM to 100 nM) in 100 µl coating buffer (100 mM Na$_2$CO$_3$, pH 9.6) with or without 1000-fold molar excess of non-labeled AgAPN2 peptides. In a competition binding assay, 20 nM of biotinylated AgAPN2 peptides were mixed with increasing concentrations of unlabeled AgAPN2 peptides. Other reaction conditions were according to Zhang et al. (2008).

Example 7

Brush Border Membrane Vesicles (BBMVs) Preparation and Binding Assays

Frozen An. gambiae 4$^{th}$ instar larvae were kindly provided by the Malaria Research and Reference Reagent Resource Center (MR4) and stored in −80° C. until use. BBMVs were prepared from whole body of 4$^{th}$ instar larvae by MgCl$_2$ precipitation according to Silva-Filha et al. (1997) and stored in aliquots at −80° C. Protein was measured by Bio-Rad protein assay using bovine serum albumin (BSA) as standard (Bradford, 1976). APN activity (Garczynski and Adang, 1995), a marker for brush border membranes, was enriched about 5-fold for the final BBMV preparation compared to the initial crude larval homogenate.

Trypsinated Cry11Ba (10 µg) was labeled with 0.5 mCi of Na$^{125}$I (PerkinElmer) using the chloramine-T method (Garczynski et al., 1991) and specific activity was 19.1 µCi/µg of input toxin. BBMV binding assays were performed according to Garczynski et al. (1991). For homologous and heterologous competition assays, duplicate samples of $^{125}$I-Cry11Ba toxin in increasing amounts were mixed with 10 µM of unlabeled APN peptides and incubated in binding buffer (20 mM Na$_2$CO$_3$, pH 9.6) at room temperature for 2 h. Samples were then added with 8 µg BBMVs that were pre-blocked for 2 h at room temperature in 25 µl of blocking buffer (20 mM Na$_2$CO$_3$, pH 9.6, 0.15 M NaCl, 0.1% Tween-20, 1.5% BSA) and then incubated at 4° C. for 18 h. Binding reactions were stopped by centrifugation and pellets washed twice with 1 ml of ice-cold binding buffer. Radioactivity of the final pellets was measured with a Beckman model Gamma 4000 detector. Each binding assay was repeated twice.

Example 8

Statistical Analysis

Sigma Plot software version 11.0 (SPSS Science, Chicago, Ill.) was used for statistical analysis of all data. Results are presented as the mean±SEM. One-way ANOVA was used to evaluate statistical significance. An asterisk symbol above the error bars indicates significant difference between means ($P<0.001$).

Example 9

AgAPN2ta and AgAPN2tb Peptides are Structurally Re-Folded in Solution

Aminopeptidase AgAPN2 was recently identified as a candidate receptor of Cry11Ba in An. gambiae larval midgut (Zhang et al., 2008). The 70-kDa peptide fragment of AgAPN2t ($^{228}$G-V$^{843}$, of SEQ ID NO:2) that binds Cry11Ba with a high affinity ($K_d$=6.4 nM) and inhibits toxicity to larvae was the starting point for this study. Towards the goal of locating Cry11Ba binding region(s) on AgAPN2t and testing for a correlation between toxin binding and toxicity inhibition, we divided AgAPN2t into segments AgAPN2ta (residues 336-590 of SEQ ID NO:2) and AgAPN2tb (residues 591-843 of SEQ ID NO:2) and expressed those peptides in E. coli (FIG. 1A). FIG. 1B shows a SDS-gel of 30-kDa AgAPN2ta and 28-kDa AgAPN2tb peptides after solubilization from inclusion bodies and purification by immobilized nickel chromatography. The peptides were dialyzed into 10 mM Na$_2$CO$_3$, pH 9.6, conditions approximating the alkaline environment of mosquito midgut, and analyzed peptide secondary structures by far-UV CD spectroscopy (FIGS. 1C and 1D). The CD spectra indicated the composition of AgAPN2ta was 34% helices, 20% β-strand, and 46% turns and random coils, while AgAPN2tb was 53% helices, 20% β-strand, and 27% turns and random coils. AgAPN2ta and AgAPN2tb fragments were partially refolded in the alkaline buffer.

Example 10

AgAPN2ta Inhibits and AgAPN2tb Enhances Cry11Ba Toxicity to An. gambiae Larvae and Both Peptides Bind Trypsinized Cry11Ba The effects of AgAPN2ta and AgAPN2tb peptides on Cry11Ba toxicity were tested by feeding fourth instar larvae of An. gambiae Cry11Ba toxin alone or in combination with AgAPN2t, -2ta or -2tb inclusion bodies. As expected from our previous study, AgAPN2t peptide blocked 98% of the Cry11Ba potency at 4 µg Cry11Ba/ml (Zhang et al., 2008). While -2ta reduced larval mortality by 85%, -2tb unexpectedly caused a slight increase in larval mortality (FIG. 2A). A 1:1 mixture of -2a and -2tb inclusions produced an intermediate level of toxicity inhibition (FIG. 2A). As shown in FIG. 2B, the enhancement effect of AgAPN2tb inclusions was significant at a low Cry11Ba concentration (0.5 µg/ml) where the addition of -2tb inclusions increased larval mortality from 11.7±4.8% to 81.7±6.5% ($P<0.001$). Peptide AgAPN2tb inclusion bodies alone were not toxic to An. gambiae larvae (FIG. 2B).

Since 70-kDa AgAPN2t binds Cry11Ba with high affinity as measured in an ELISA microplate binding assay, we tested binding of AgAPN2ta and -2tb peptides in the same saturation binding format (Zhang et al., 2008). Plates were coated with trypsinized Cry11Ba and probed with biotin-AgAPN2ta or biotin-AgAPN2tb peptide alone or with excess unlabeled homologous peptide (FIG. 3A and FIG. 3B). Using a one-site saturation fit model, the calculated $K_d$ for AgAPN2ta binding to Cry11Ba was 16.7±4.8 nM and $K_d$=26.4±3.6 nM for -2tb peptide. Although both truncated AgAPN2t peptides bound toxin, the affinities were lower than the affinity ($K_d$=6.4±1.4 nM) previously determined for 70-kDa AgAPN2t binding to Cry11Ba (Zhang et al., 2008).

Reasoning that AgAPN2ta and -2tb peptides may bind distinct sites on Cry11Ba we biotinylated AgAPN2ta and AgAPN2tb and measured binding to immobilized Cry11Ba alone and in the presence of increasing concentrations (5 nM-20 µM) of unlabeled homologous or heterologous peptides. As shown in FIGS. 3C and 3D the competition curves are similar for biotin-AgAPN2a and -AgAPN2b probes and for homologous and heterologous competitors, a result indicative of a shared binding site or sites on Cry11Ba.

Example 11

Toxicity Inhibition Depends on Cry11Ba Binding to the N-Terminal Region of AgAPN2ta The correlation between AgAPN2ta inhibition of Cry11Ba toxicity and toxin binding was tested by producing in-frame truncations that deleted 10-kDa segments of AgAPN2ta resulting in the 20-kDa peptides AgAPN2ta/Del1, -2ta/Del2 and -2ta/Del3 (FIG. 4A). FIG. 4B shows a stained SDS-gel of peptides after partial purification from E. coli inclusion bodies. Cry11Ba was fed alone to larvae or with a 1:100 ratio of AgAPN2ta or deleted peptide inclusion bodies and mortality was scored after 24 hours. Peptide AgAPN2ta inclusion bodies reduced larval mortality from 93.8±3.2 to 13.8±4.6% (P<0.001), and peptides -2ta/Del2 and -2ta/Del3 reduced mortality to 8.8±4.0% and 5.0±2.7%, respectively. The addition of AgAPN2ta/Del1 inclusion bodies did not alter Cry11Ba toxicity, indicating that the N-terminal 10-kDa of AgAPN2ta ($^{336}$S-P$^{420}$) is critical to AgAPN2ta inhibition of Cry11Ba toxicity (FIG. 4C).

Since biotin-AgAPN2ta binds Cry11Ba in a specific and competitive manner we tested the abilities of each deleted AgAPN2ta peptide to compete binding in an ELISA. While 20 nM input biotin-AgAPN2ta was displaced by increased concentrations (5 nM-20 µM) of unlabeled AgAPN2ta, -2ta/Del2 and -2ta/Del3 (FIG. 5A), AgAPN2ta/Del1 was less effective at reducing bound biotin-AgAPN2ta. The result that AgAPN2ta/Del1 reduced biotin-AgAPN2ta binding to about half that of the other AgAPN2ta peptides suggested the removal of a binding site from AgAPN2ta by the Del1 deletion and that a second binding site(s) is contained in regions 2 and 3 of AgAPN2ta. Further evidence of loss of a Cry11Ba binding site in AgAPN2ta/Del1 is shown in FIG. 5B where AgAPN2ta/Del1 at a 1000-fold ratio to biotin-AgAPN2ta minimally reduced binding to Cry11Ba in a saturation assay.

Since AgAPN2t reduced $^{125}$I-Cry11Ba binding to BBMV prepared from An. gambiae larvae (Zhang et al., 2008), we tested AgAPN2ta and its deleted versions as competitors of $^{125}$I-Cry11Ba binding to BBMV. Unlabeled 70-kDa AgAPN2t fragment competed 54.6% of the $^{125}$I-Cry11Ba binding, reducing the toxin bound from 27.86±1.03 fmole to 12.65±0.92 fmole. The 30-kDa AgAPN2ta peptide and the deleted peptides -2a/Del2 and -2a/Del3 reduced bound Cry11Ba to 19.95±1.44 fmole, 20.59±0.76 fmole for -2ta/Del2 and 19.51±0.90 fmole, respectively. In contrast, the addition of AgAPN2ta/Del1, the peptide with the deleted Cry11Ba binding site did not change $^{125}$I-Cry11Ba binding.

AgAPN2ta/Del1 peptide with residues $^{336}$S-P$^{420}$ of AgAPN2 deleted had lost a Cry11Ba binding site, the ability to compete Cry11Ba binding to BBMV and the ability to reduce Cry11Ba toxicity to An. gambiae larvae. These results are evidence that residues $^{336}$S-P$^{420}$ contain an epitope that is critical for Cry11Ba binding to aminopeptidase AgAPN2.

Example 12

Figure 2:
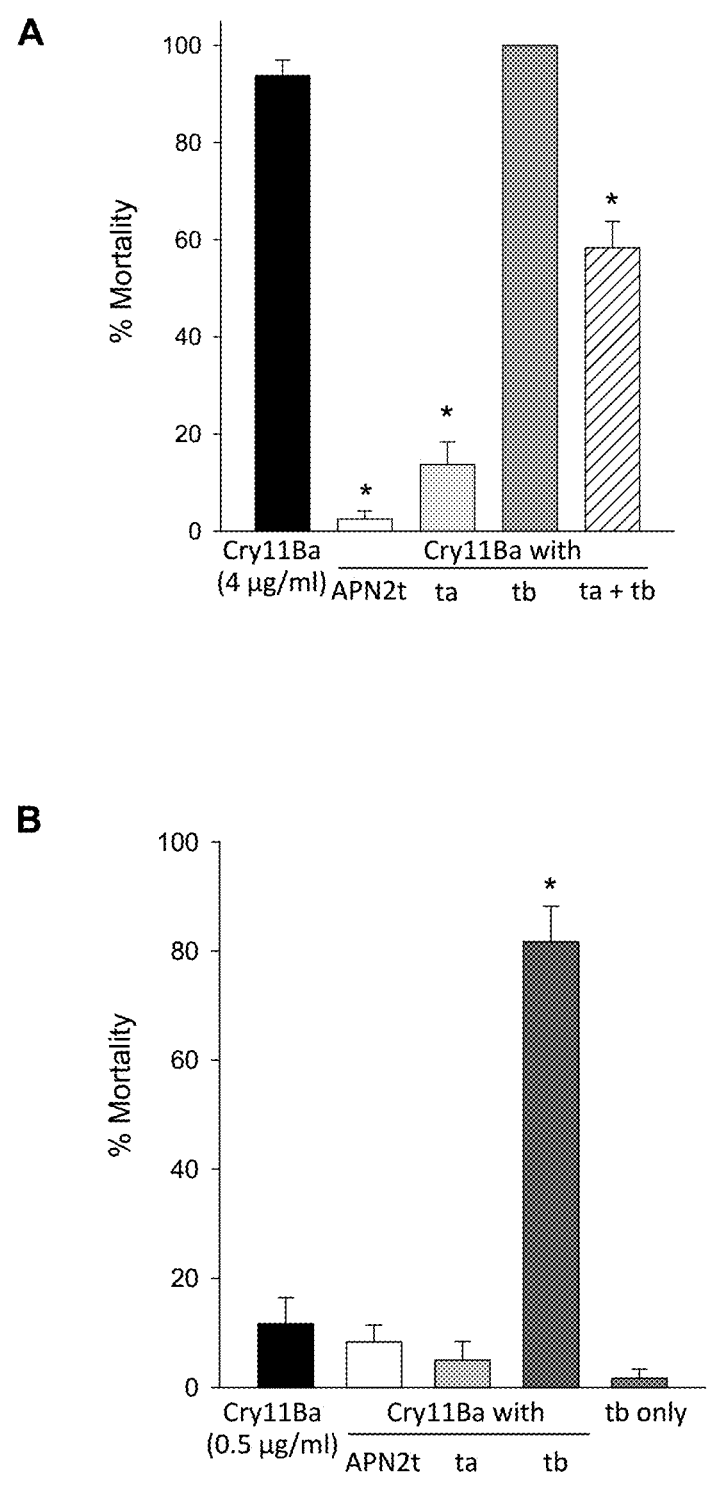
Figure 3:
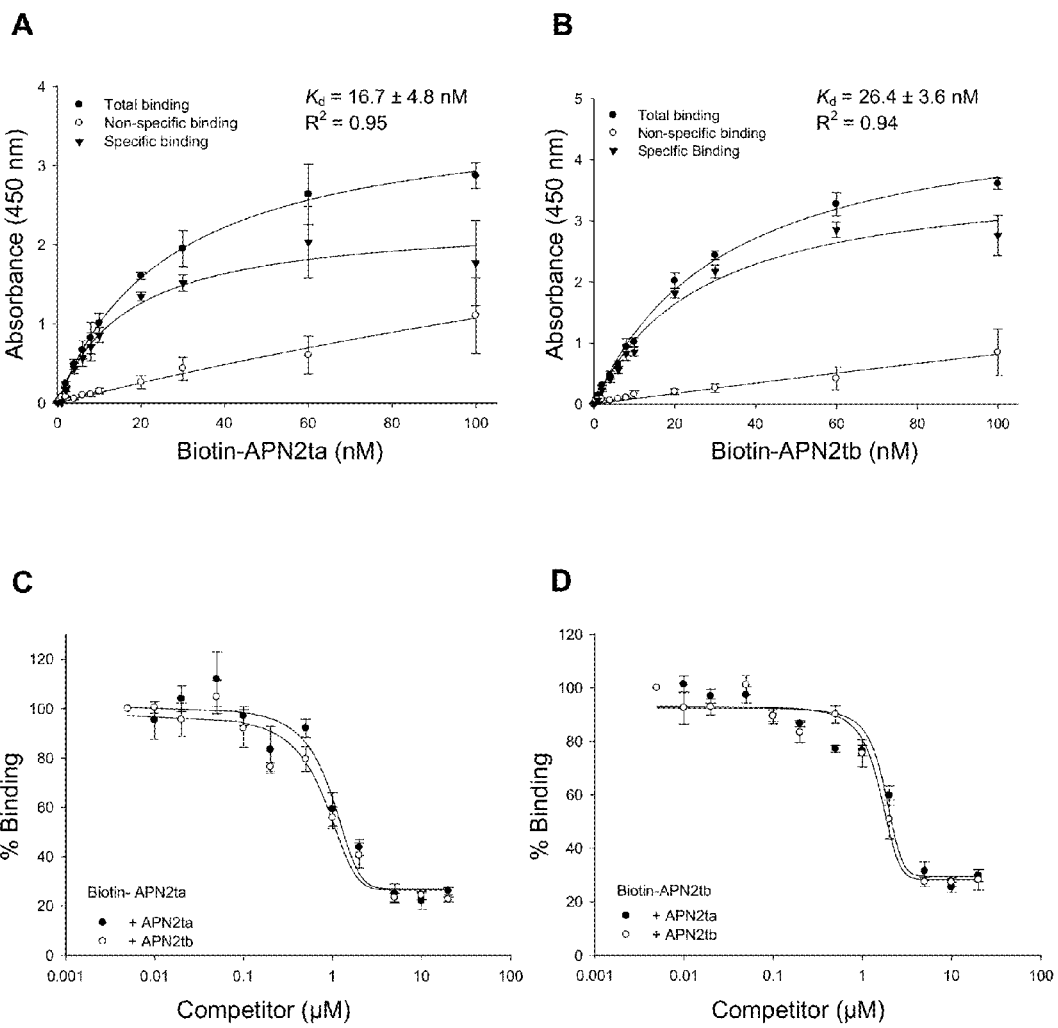
FIG. 3: Analyses of the interaction between Cry11Ba and truncated APN peptides. The binding affinities ($K_d$) of AgAPN2ta (FIG. 3(A)) or AgAPN2tb (FIG. 3(B)) to Cry11Ba were determined by saturation binding assays using increasing nM concentrations of biotinylated peptides with 1000-fold molar excess of unlabeled homologous peptides.

Toxicity Enhancement is Correlated with a Central 10-kDa Region of AgAPN2tb and Increased 125I-Cry11Ba Binding to BBMV As shown in FIGS. 2 and 3, AgAPN2tb bound Cry11Ba with high affinity and enhanced Cry11Ba toxicity. In-frame deleted peptides of AgAPN2tb were constructed to identify a region of AgAPN2tb critical to enhancement of Cry11Ba toxicity. Peptides AgAPN2tb/Del1, -2tb/Del2 and -2tb/Del3 had fragments deleted from the N-terminal ($^{591}$G-I$^{661}$), middle ($^{676}$I-W$^{760}$), or C-terminal ($^{761}$N-V$^{843}$) region, respectively, of AgAPN2tb (FIG. 6A and FIG. 6B). Cry11Ba alone at 0.5 µg/ml killed 10.0±2.6% of the An. gambiae larvae. When the same amount of toxin was mixed with 100-fold excess AgAPN2tb, larval mortality attained 82.7±6.5%. The addition of 100-fold -2tb/Del1 or -2tb/Del3 also caused a significant toxicity enhancement (P<0.001) to 61.7±4.9% and 76.7±6.7% mortality, respectively. In contrast, AgAPN2tb/Del2 peptide added to Cry11Ba resulted in 18.0±4.9% mortality, a level not statistically different from Cry11Ba alone (FIG. 6C). These results demonstrated that the middle region of AgAPN2tb ($^{676}$I-W$^{760}$) was essential for the enhancing effect mediated by AgAPN2tb peptide.

To locate the toxin binding region in AgAPN2tb, we coated microtiter plate wells with Cry11Ba and probed with biotin-AgAPN2tb alone or with increased concentrations (5 nM-20 µM) of unlabeled AgAPN2tb or its deletions. FIG. 7A shows the results of the competition binding experiment where -2tb/Del2 displaced biotinylated AgAPN2tb binding to a level similar to that of unlabeled AgAPN2tb, whereas -2tb/Del1 and -2tb/Del3 only partially competed binding of AgAPN2tb. A deletion in the middle region of AgAPN2tb did not alter the binding to Cry11Ba while deletions in either end resulted in the partial loss of toxin binding, suggesting that Cry11Ba binding sites are localized on both N-terminal and C-terminal regions of AgAPN2tb.

AgAPN2tb/Del2 had lost the ability to enhance Cry11Ba toxicity yet bound Cry11Ba to the same extent as AgAPN2tb. We hypothesized that AgAPN2tb might affect Cry11Ba binding to BBMV. Therefore we measured $^{125}$I-Cry11Ba binding to BBMV in the presence of AgAPN2tb or it deleted derivatives. As shown in FIG. 7C, AgAPN2tb, -2tb/Del1 and -2tb/Del3 increased Cry11Ba binding to BBMV by 24%, 62% and 45%, respectively. In contrast, binding of $^{125}$I-Cry11Ba to BBMV was decreased 50% with 70-kDa AgAPN2t and 72% with 18-kDa AgAPN2tb/Del2.

In summary, in bioassay experiments AgAPN2tb, -2tb/Del1 and -2tb/Del3 enhanced Cry11Ba toxicity to larvae and the same peptides bound Cry11Ba and increased $^{125}$I-Cry11Ba binding to BBMV. In contrast the deleted peptide AgAPN2tb/Del2 bound Cry11Ba, but reduced Cry11Ba binding to BBMV and had no effect on toxicity. Although the central region of AgAPN2tb is not involved in peptide binding to Cry11Ba, the region is necessary for increased Cry11Ba binding to BBMV and increased Cry11Ba toxicity to larvae.

REFERENCES

Boonserm, P., Davis, P., Ellar, D. J., Li, J., 2005. Crystal structure of the mosquito-larvicidal toxin Cry4Ba and its biological implications. J. Mol. Biol. 348, 363-382.

Boonserm, P., Mo, M., Angsuthanasombat, C., Lescar, J., 2006. Structure of the functional form of the mosquito larvicidal Cry4Aa toxin from Bacillus thuringiensis at a 2.8-Angstrom Resolution. J. Bacteriol. 188, 3391-3401.

Bradford, M., 1976. A rapid and sensitive method for the quantitation of microgram quantities of protein utilizing the principle of protein-dye binding. Anal. Biochem. 72, 248-254.

Bravo, A., Gomez, I., Conde, J., Muñoz-Garay, C., Sanchez, J., Miranda, R., Zhuang, M., Gill, S. S., Soberón, M., 2004. Oligomerization triggers binding of a Bacillus thuringiensis Cry1Ab pore-forming toxin to aminopeptidase N receptor leading to insertion into membrane microdomains. Biochim. Biophys. Acta 1667, 38-46.

Burton, S. L., Ellar, D. J., Li, J., Derbyshire, D. J., 1999. N-acetylgalactosamine on the putative insect receptor aminopeptidase N is recognised by a site on the domain III lectin-like fold of a *Bacillus thuringiensis* insecticidal toxin. J. Mol. Biol. 287, 1011-1022.

Chen, J., Aimanova, K. G., Pan, S., Gill, S. S., 2009. Identification and characterization of *Aedes aegypti* aminopeptidase N as a putative receptor of *Bacillus thuringiensis* Cry11A toxin. Insect Biochem. Mol. Biol. 39, 688-696.

Chen, J., Hua, G., Jurat-Fuentes, J. L., Abdullah, M. A., Adang, M. J., 2007. Synergism of *Bacillus thuringiensis* toxins by a fragment of a toxin-binding cadherin. Proc. Natl. Acad. Sci. USA 104, 13901-13906.

Delécluse, A., Rosso, M. L., Ragni, A., 1995. Cloning and expression of a novel toxin gene from *Bacillus thuringiensis* subsp *jegathesan* encoding a highly mosquitocidal protein. Appl. Environ. Microbiol. 61, 4230-4235.

Galitsky, N., Cody, V., Wojtczak, A., Ghosh, D., Luft, J. R., Pangborn, W., English, L., 2001. Structure of the insecticidal bacterial delta-endotoxin Cry3Bb1 of *Bacillus thuringiensis*. Acta Cryst. D57, 1101-1109.

Garczynski, S. F., Adang, M. J., 1995. *Bacillus thuringiensis* CryIA(c) δ-endotoxin binding aminopeptidase in the *Manduca sexta* midgut has a glycosyl-phosphatidylinositol anchor. Insect Biochem. Mol. Biol. 25, 409-415.

Garczynski, S. F., Crim, J. W., Adang, M. J., 1991. Identification of putative insect brush border membrane-binding molecules specific to *Bacillus thuringiensis* delta-endotoxin by protein blot analysis. Appl. Environ. Microbiol. 57, 2816-2820.

Grochulski, P., Masson, L., Borisova, S., Pusztai-Carey, M., Schwartz, J.-L., Brousseau, R., Cygler, M., 1995. *Bacillus thuringiensis* CryIA(a) insecticidal toxin: crystal structure and channel formation. J. Mol. Biol. 254, 447-464.

Hua, G., Jurat-Fuentes, J. L., Adang, M. J., 2004. Bt-$R_{1a}$ extracellular cadherin repeat 12 mediates *Bacillus thuringiensis* Cry1Ab binding and cytotoxicity. J. Biol. Chem. 279, 28051-28056.

Jenkins, J. L., Lee, M. K., Valaitis, A. P., Curtiss, A., Dean, D. H., 2000. Bivalent sequential binding model of a *Bacillus thuringiensis* toxin to gypsy moth aminopeptidase N receptor. J. Biol. Chem. 275, 14423-14431.

Lacey, L. A., 2007. *Bacillus thuringiensis* serovariety *israelensis* and *Bacillus sphaericus* for mosquito control. J. Am. Mosq. Control Assoc. 23, 133-163.

Li, J., Carroll, J., Ellar, D. J., 1991. Crystal structure of insecticidal δ-endotoxin from *Bacillus thuringiensis* at 2.5 Å resolution. Nature 353, 815-821.

Lobley, A., Whitmore, L., Wallace, B. A., 2002. DICHROWEB: an interactive website for the analysis of protein secondary structure from circular dichroism spectra. Bioinformatics 18, 211-212.

Luo, K., Sangadala, S., Masson, L., Mazza, A., Brousseau, R., Adang, M. J., 1997. The *Heliothis virescens* 170-kDa aminopeptidase functions as 'Receptor A' by mediating specific *Bacillus thuringiensis* Cry1A δ-endotoxin binding and pore formation. Insect Biochem. Mol. Biol. 27, 735-743.

Masson, L., Lu, Y. J., Mazza, A., Brousseau, R., Adang, M. J., 1995. The CryIA(c) receptor purified from *Manduca sexta* displays multiple specificities. J. Biol. Chem. 270, 20309-20315.

Morse, R. J., Yamamoto, T., Stroud, R. M., 2001. Structure of Cry2Aa suggests an unexpected receptor binding epitope. Structure (Camb) 9, 409-417.

Nakanishi, K., Yaoi, K., Nagino, Y., Hara, H., Kitami, M., Atsumi, S., Miura, N., Sato, R., 2002. Aminopeptidase N isoforms from the midgut of *Bombyx mori* and *Plutella xylostella*—their classification and the factors that determine their binding specificity to *Bacillus thuringiensis* Cry1A toxin. FEBS Lett. 519, 215-220.

Nakanishi, K., Yaoi, K., Shimada, N., Kadotani, T., Sato, R., 1999. *Bacillus thuringiensis* insecticidal Cry11Aa toxin binds to a highly conserved region of aminopeptidase N in the host insect leading to its evolutionary success. Biochim. Biophys. Acta 1432, 57-63.

Pacheco, S., Gómez, I., Arenas, I., Saab-Rincon, G., Rodríguez-Almazán, C., Gill, S. S., Bravo, A., Soberón, M., 2009a. Domain II loop 3 of *Bacillus thuringiensis* Cry1Ab toxin is involved in a "ping pong" binding mechanism with *Manduca sexta* aminopeptidase-N and cadherin receptors. J. Biol. Chem. 284, 32750-32757.

Pacheco, S., Gómez, I., Gill, S. S., Bravo, A., Soberón, M., 2009b. Enhancement of insecticidal activity of *Bacillus thuringiensis* Cry1A toxins by fragments of a toxin-binding cadherin correlates with oligomer formation. Peptides 30, 583-588.

Park, Y., Abdullah, M. A., Taylor, M. D., Rahman, K., Adang, M. J., 2009a. Enhancement of *Bacillus thuringiensis* Cry3Aa and Cry3Bb toxicities to Coleopteran larvae by a toxin-binding fragment of an insect cadherin. Appl. Environ. Microbiol. 75, 3086-3092.

Park, Y., Hua, G., Abdullah, M. A. F., Rahman, K., Adang, M. J., 2009b. Cadherin fragments from *Anopheles gambiae* synergize *Bacillus thuringiensis* Cry4Ba's toxicity against *Aedes aegypti* larvae. Appl. Environ. Microbiol. 75, 7280-7282.

Peng, D., Xu, X., Ye, W., Yu, Z., Sun, M., 2010. *Helicoverpa armigera* cadherin fragment enhances Cry1Ac insecticidal activity by facilitating toxin-oligomer formation. Appl. Microbiol. Biotechnol. 85, 1033-1040.

Pigott, C. R., Ellar, D. J., 2007. Role of receptors in *Bacillus thuringiensis* crystal toxin activity. Microbiol. Mol. Biol. Rev. 71, 255-281.

Porter, A. G., Davidson, E. W., Liu, J. W., 1993. Mosquitocidal toxins of bacilli and their genetic manipulation for effective biological control of mosquitoes. Microbiol. Rev. 57, 838-861.

Silva-Filha, M. H., Nielsen-Leroux, C., Charles, J.-F., 1997. Binding kinetics of *Bacillus sphaericus* binary toxin to midgut brush-border membranes of *Anopheles* and *Culex* sp. mosquito larvae. Eur. J. Biochem. 247, 754-761.

Soberón, M., Pardo-Lopez, L., Lopez, I., Gómez, I., Tabashnik, B. E., Bravo, A., 2007. Engineering modified Bt toxins to counter insect resistance. Science 318, 1640-1642.

Valaitis, A. P., Mazza, A., Brousseau, R., Masson, L., 1997. Interaction analyses of *Bacillus thuringiensis* Cry1A toxins with two aminopeptidases from gypsy moth midgut brush border membranes. Insect Biochem. Mol. Biol. 27, 529-539.

Whitmore, L., Wallace, B. A., 2004. DICHROWEB, an online server for protein secondary structure analyses from circular dichroism spectroscopic data. Nucleic Acids Res. 32, W668-673.

Whitmore, L., Wallace, B. A., 2008. Protein secondary structure analyses from circular dichroism spectroscopy: methods and reference databases. Biopolymers 89, 392-400.

Yaoi, K., Nakanishi, K., Kadotani, T., Imamura, M., Koizumi, N., Iwahana, H., Sato, R., 1999. *Bacillus thuringiensis* Cry1Aa toxin-binding region of *Bombyx mori* aminopeptidase N. FEBS Lett. 463, 221-224.

Zhang, R., Hua, G., Andacht, T. M., Adang, M. J., 2008. A 106-kDa aminopeptidase is a putative receptor for *Bacillus thuringiensis* Cry11Ba toxin in the mosquito *Anopheles gambiae*. Biochemistry 47, 11263-11272.

Zhang, X., Candas, M., Griko, N. B., Taussig, R., Bulla, L. A., Jr., 2006. A mechanism of cell death involving an adenylyl cyclase/PKA signaling pathway is induced by the Cry1Ab toxin of *Bacillus thuringiensis*. Proc. Natl. Acad. Sci. USA 103, 9897-9902.

The invention claimed is:

1. A method of inhibiting mosquitos, said method comprising providing to said mosquito for ingestion, a mixture comprising *Bacillus* Cry11Ba protein and a polypeptide that is residues 591-843 of SEQ ID NO:2, wherein said polypeptide binds said Cry11Ba protein and enhances mosquitocidal activity of said Cry11Ba protein.

* * * * *

UNITED STATES PATENT AND TRADEMARK OFFICE
CERTIFICATE OF CORRECTION

| | |
|---|---|
| PATENT NO. | : 9,215,869 B1 |
| APPLICATION NO. | : 13/090830 |
| DATED | : December 22, 2015 |
| INVENTOR(S) | : Michael J. Adang et al. |

It is certified that error appears in the above-identified patent and that said Letters Patent is hereby corrected as shown below:

On the Title page, item (54) and in the Specification, column 1 please change the title from NON-CADHERIN POLYPEPTIDE POTENTITATORS OF CRY PROTEINS to NON-CADHERIN POLYPEPTIDE POTENTIATORS OF CRY PROTEINS Signed and Sealed this
Fifth Day of April, 2016

Michelle K. Lee
*Director of the United States Patent and Trademark Office*